(12) United States Patent
Weber et al.

(10) Patent No.: US 7,081,118 B2
(45) Date of Patent: Jul. 25, 2006

(54) MEDICAL TOOL

(76) Inventors: Helmut Weber, Enginer Strasse 11, 78576 Emmingen-Liptingen (DE); Bernd Daniels, Johannasberg 22, 42799 Leichlingen (DE)

(*) Notice: Subject to any disclaimer, the term of this patent is extended or adjusted under 35 U.S.C. 154(b) by 0 days.

(21) Appl. No.: 10/225,763

(22) Filed: Aug. 22, 2002

(65) Prior Publication Data
US 2004/0039397 A1 Feb. 26, 2004

(51) Int. Cl.
*A61B 17/58* (2006.01)

(52) U.S. Cl. ...................................... 606/90

(58) Field of Classification Search ................ 606/90, 606/61, 99, 105, 190, 193, 205, 206, 207, 606/208, 57; 600/216, 218, 219, 222, 225, 600/235; 81/427.5, 352, 353, 354, 362, 423, 81/426, 177.1
See application file for complete search history.

(56) References Cited

U.S. PATENT DOCUMENTS

| | | | | | |
|---|---|---|---|---|---|
| 332,597 | A | * | 12/1885 | Donovan | 30/349 |
| 632,843 | A | * | 9/1899 | McGhee | 433/159 |
| 1,940,855 | A | | 12/1933 | Friedman | |
| 4,711,240 | A | * | 12/1987 | Goldwasser et al. | 606/174 |
| 5,527,339 | A | | 6/1996 | Kischer et al. | |
| 5,931,777 | A | | 8/1999 | Sava | |
| 6,017,342 | A | * | 1/2000 | Rinner | 606/57 |
| 6,108,845 | A | * | 8/2000 | Hung et al. | 7/128 |
| 6,261,296 | B1 | * | 7/2001 | Aebi et al. | 606/90 |
| 6,370,991 | B1 | * | 4/2002 | Hsieh | 81/427.5 |
| 6,551,316 | B1 | * | 4/2003 | Rinner et al. | 606/57 |
| 6,663,562 | B1 | * | 12/2003 | Chang | 600/219 |
| 2001/0031969 | A1 | | 10/2001 | Aebi et al. | |
| 2002/0019637 | A1 | | 2/2002 | Frey et al. | |

FOREIGN PATENT DOCUMENTS

| | | |
|---|---|---|
| DE | 199 18 638 C | 9/2001 |
| EP | 0 780 093 B1 | 2/2003 |

* cited by examiner

*Primary Examiner*—Pedro Philogene
(74) *Attorney, Agent, or Firm*—Akerman Senterfitt; Stephen A. Pendorf

(57) ABSTRACT

The invention concerns a medical tool, in particular a vertebral distractor (1), with a first (2) and a second link part (3), wherein the first link part (2) is connected with the second link part (3) via a rotation axis (4), and therein a grip element (6,8) and a pliers element (5,7) is provided on each link part (2,3), which are operatively associated with each other, and wherein the two grip elements (6,8) are provided on a first side relative to the rotation axis (4) and the two pliers elements (5,7) are provided on a second side lying opposite to the first side, and wherein a valve (12) is seatable in the area of the free axial ends of a pliers element (5,7) and releaseably connected by a securing mechanism of the first type, and wherein a push button of the first type (14) is provided on the securing mechanism of the first type.

29 Claims, 5 Drawing Sheets

MEDICAL TOOL

BACKGROUND OF THE INVENTION

1. Field of the Invention

The invention concerns a medical tool, in particular a vertebral distractor, of the type according to the precharacterizing portion of patent claim 1.

2. Description of the Related Art

Distractors are employed in surgery, where it is necessary to change the separation between two parts of the spinal parts, in particular, to increase the separation. A vertebral distractor has the task of increasing the separation of two vertebrae, in particular during an operational procedure in the area of the vertebral disks. A distractor is essentially comprised of two pliers-shaped link elements, with grip parts and with engagement parts in the form of jaws. If the engagement parts can be changed out, they are referred to as "valves". The valves are in operating engagement with the grip elements. For spreading apart two vertebra of the spinal column, the distractor with the two valves is introduced between the vertebra to be spread apart. Spreading occurs by operation of the grip elements. The degree of spreading between the valves can be set by an adjustment element.

U.S. Pat. No. 6,017,342 discloses vertebral distractors comprised of two link parts. Each link part includes a grip element as well as a jaw. The two link parts are connected rotatably in the area between the grip parts and the jaws. According to this reference, the degree of opening of the two jaws is fixed using an adjustment screw, which is connected with the linkage parts in the area of the grip elements via a linkage mechanism.

U.S. Pat. No. 2002,0,019,637 A1 discloses a distractor with fold-back grip elements. Thereby it becomes possible, after a successful spreading of two vertebra, to fold the projecting grip elements, which essentially interfere with the operation, back along the plane of the body to be operated upon.

Also known in the art are vertebral distractors with exchangeable jaws. The valves are either connected with the pliers' elements associated with the linkage part via a screw connection, or however are secured on the pliers element via a detent or locking mechanism. In the first case, in order to change the valves, the screw connection must be undone using a tool. In the second case also a tool is necessary for releasing the locking connection. Accordingly it can be seen that a change-out of the valves of a distractor during a surgical intervention is almost impossible, whereby the multi-facetted usefulness of the tool is substantially reduced. Vertebral distractors with the above-described blocking mechanism are shown on the home page of Fa. Beere Medical Precision Instruments at the site www.beeremedical.com/pages/comdist.htm. Further, in the case of vertebral distractors with change out valves, there is the requirement that the forces exerted upon the pliers elements via the valves must be transmitted without free play.

SUMMARY OF THE INVENTION

The present invention is thus concerned with the task of providing a distractor of the above-described type, in which the valves are exchangeable in simple mode and manner.

This task is solved with a distractor having the characterizing features of claim 1.

Preferred embodiments of the invention can be found in the characterizing features of the dependent claims.

The invention is based upon the idea of providing, in a securing mechanism of first type, via which a valve is releasably secured in the area of the free axial end of a pliers element, a push-button of a first type, by which the securing between valve and pliers element is releasable. In this mode and manner it is possible, by operation of the push-button of the first type, to release the connection between valve and pliers element without tools in simple mode and manner. Thereby it is possible, while in place at the location of use during a surgical intervention, to rapidly and simply switch between valves of various designs and functions depending upon requirements.

It is irrelevant in accordance with the principle of the invention whether the push-button of the first type is provided on the pliers elements or on the valve.

In order to keep the handling during changing out of the valves particularly simple, it is preferred when the two push-buttons of the first type are provided on opposite sides of the two pliers elements. Thereby it becomes possible, using two fingers of one hand, such as for example the thumb and index finger, to operate both push-buttons, whereby the other hand remains free for removing and applying the valves to be changed out.

A particularly desirable embodiment of the invention with regard to construction is comprised therein, when the securing mechanism of the first type comprises an engagement element as well as a locking element in operative association with the push-button of the first type. Herein, securing is accomplished by engagement of the locking element in the engagement element. Further, the locking element is held in the securing position by the spring element.

A further preferred embodiment of the invention is comprised therein, that the engagement element as well as the push-button of the first type is provided on the valve, and the locking element with spring is provided on the pliers element.

A particularly simple to produce, space saving and robust locking mechanism results when the push-button and the locking element are one integral unit.

A further constructively simple and thus particularly preferred embodiment is comprised therein, when the valve can be pushed into a recess in the pliers element essentially via the engagement element.

In order to precisely position the valve in the pliers element, it is useful when an abutment surface is provided on the pliers element and a counter-surface is provided on the valve, such that the abutment of these surfaces determines the maximal insertion depth of the valve in the pliers element.

In order to secure the valve without play on the pliers element it is useful when the locking element of the pliers element and the engagement element of the valve, beginning with a certain insertion position, engage with each other in such a manner, that the valve, in response to a force acting in the insertion direction is moved in the insertion direction, and the counter-surface is brought to bear against the abutment surface of the pliers element.

According to a particularly preferred embodiment, the engagement element is fork-shaped in the longitudinal direction with an arc shaped segment and the locking element is at least partially in the form of a cone. Further, the cone, when abutting against the counter-surface of the abutment surface, is segment-wise brought into operative association with a clamping surface of the circular or arch shaped segment, whereby the longitudinal axis of the locking element is provided setoff in the insertion direction relative to the center point of the arch shaped segment.

Since high forces act on the valves, and following therefrom, on the pliers element, both the valves as well as the segments between the components must be designed for accommodating high forces. By the design of the engagement elements of the valve in the shape of a fork and corresponding design of the recess on the pliers element for form-fitting receiving of the fork shaped engagement element, a large contact surface in the area of the segment between valve and pliers elements is realized. Thereby locally high torque in the area of the sections is avoided and close tolerance perpendicular to the direction of insertion of the grip element is connected to the linkage part by means of engagement element in the recess is ensured. By the arc shaped segment at the engagement element in which the locking element engages as described above, the close tolerance between the valve and pliers element in the direction insertion of the valve in the pliers element is realized.

In order to provide unimpeded access in the area to be treated during further operational intervention it is preferred, following the successful increasing of the distance between vertebra, when at least one a releasable securing mechanism of the second type.

In order to release the grip element in simple manner from the linkage part, it is useful, when on the securing mechanism of the second type is in the form of a push-button of the second type.

In order to save the operator during operation from having to switch between various manipulative movements of the securing mechanisms, it is useful when the securing mechanism of the second type has a design similar to the securing mechanism of the first type. It is also advantageous for manufacturing reasons during the production of the distractor, to construct the two securing mechanisms with the same elements. This also saves on assembly and manufacturing costs. It is further advantageous for maintaining a supply inventory of spare parts, when the securing mechanisms for securing the valves and the grip element on the pliers element and the linkage elements are the same.

A further advantageous embodiment of the invention is comprised therein, that at least one grip element is pivotably connected with the linkage part. Here also the advantage lies therein, that by folding back of the grip element in the plane of the body operated upon the accessibility to the site of operation is improved. Further, depending upon the respective position of the tool to be body being operated upon, the likelihood that the operator becomes hung up on the tool is reduced.

For working with the distractor, in particular for the spreading apart of bones, it is necessary that the grip element is rigidly connected with the linkage part. After the bones have been spread apart, it is advantageous, when the grip element is moveable pivotably relative to the linkage part. For this reason it is advantageous to provide the grip element pivotably on the linkage part via a locking mechanism, whereby the locking mechanism can be brought from a first position, in which the grip element and the linkage element are connected pivotably relative to each other, into a second position, in which the grip element and the linkage part are rigidly connected with each other.

In order to operate the locking element in simple mode and manner, it is advantageous, when the locking element is operable via a push button of the third type.

The manipulation of the push buttons of the second and third type, in the sense of a one-handed operation by the operator, is particularly facilitated when the two push buttons of the second or third type are provided on opposite sides of the two grip elements or the linkage element. In order to provide the operator with the same tactile feeling for all securing and locking mechanisms, it is useful when the push button of the first, second or third type are of the same design, and when these are operable in the same mode and manner.

For fixing the opening or spreading angle of the linkage part or, as the case may be, the valves, it is useful to provide an adjustment mechanism, by which the opening angle can be set.

In particular in the case of distractors with fold back or removable grip elements it is useful, when the adjustment element is provided in the area of the linkage part, in particular when the adjustment element connects the linkage parts with each other. Thereby in the case of folded-back grip elements a constant remaining angular position of the linkage elements or as the case may be valves is possible simply by providing the adjustment mechanism in the area of the linkage part. In the case of a distractor with removable grip elements, a maintaining constant of the angular position of the valves can only be guaranteed when the adjustment element is not provided in the area of the grip elements.

A preferred embodiment is comprised therein, that the adjustment element is in the form of an adjusting nut with threaded shaft.

In order to make possible a one-handed operation of the grip elements during closing and during opening, it is useful to provide a pressure spring, by mean of which the grip elements are urged apart. As a result, the grip elements can be closed with one hand by pressing, and the force necessary for opening of the grip elements, which in the present design of the grip elements requires application of a pull force which cannot easily be applied by the user, is applied by the compression spring. As a result, the grip elements remain in contact with the hand of the user during opening and closing of the grip elements.

A further preferred embodiment is comprised therein, to provide a scissors-part in the area of the pliers elements, by means of which the pliers elements running parallel to each other when spreading.

BRIEF DESCRIPTION OF THE DRAWING

The invention will now be described in greater detail on the basis of the embodiment represented schematically in the figures. There is shown.

DETAILED DESCRIPTION OF THE INVENTION

Figure 1:
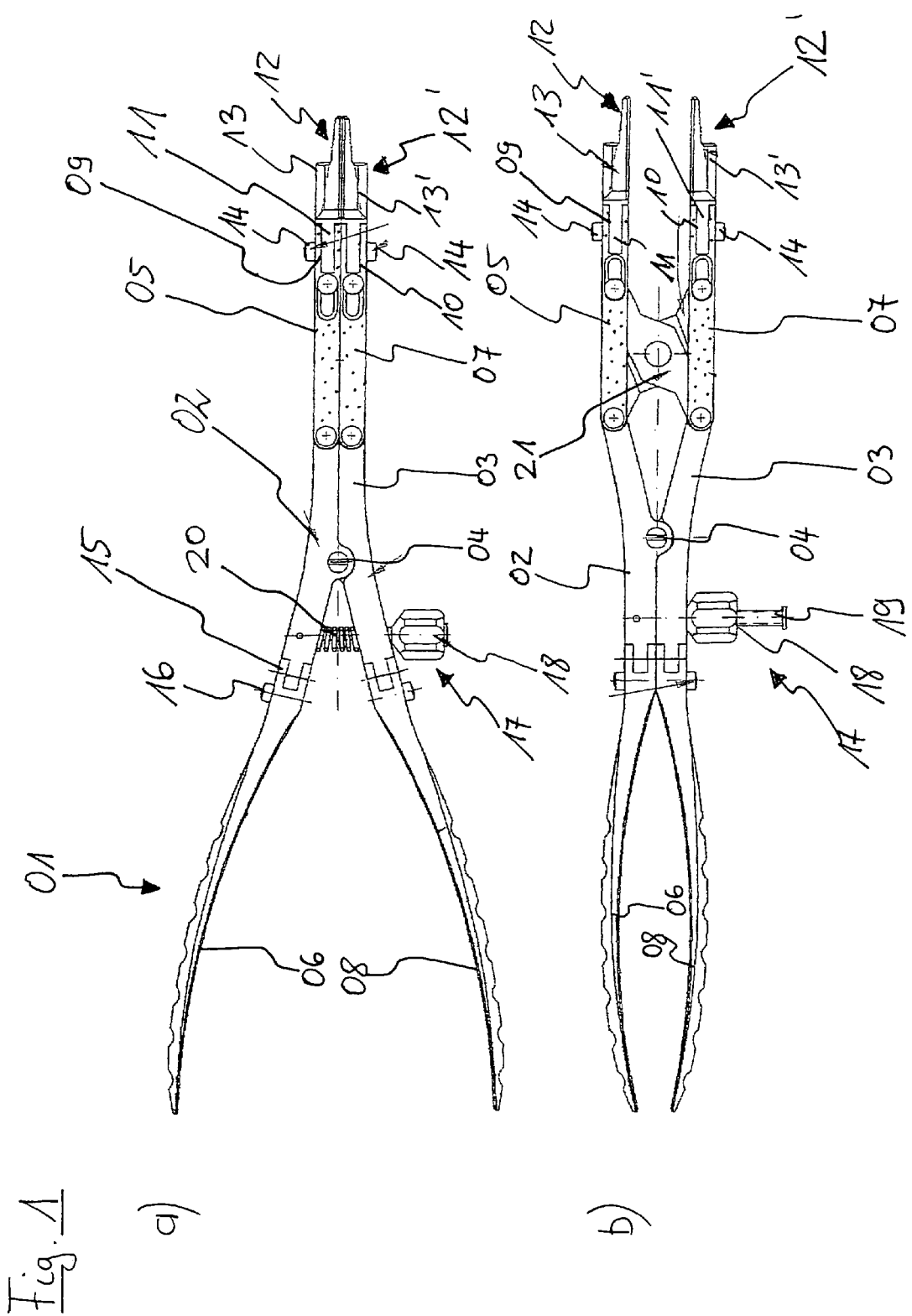
FIG. 1 a vertebral distractor in side view with closed or as the case may be opened pliers elements.

FIG. 1a shows a vertebral distractor 01 comprised of a first link part 02, which is pivotably connected with a second link part 03. The pivotably linkage between the first link part 02 and the second link part 03 is achieved by a connecting pin 04, which at the same time defines the axis of rotation 04. The first link part 02 is provided with a pliers element 05 as well as a grip element 06. The second link element is provided with a pliers element 07 as well as a grip part 08. With reference to the axis of rotation 04 defined by the connecting pin 04 between the two linkage parts 02 and 03, the grip elements 06, 08 are provided on a first side. With reference to the axis of rotation defined by the connecting pin 04, the pliers elements 05, 07 are provided on a second side lying opposite to the first side. The pliers element 05 is in operative association with the grip part 06 via the first link part 02. The pliers element 07 is operatively associated with the grip element 08 via the second link part 03. On the two free axial ends of the pliers elements 05, 07 there are provided recesses 09, 10. In the recesses 09 and 10 there is respectively insertable one engagement element 11 of a valve 12. Each valve is comprised of an engagement element 11 and a jaw 13. The valve 12 is releasably securable on the respective pliers element 05, 07 via a securing mechanism of the first type (for reasons of better oversight, the securing mechanism of the first type is separately shown in FIG. 2 and thus the details of the securing mechanism of the first type are not shown in FIG. 1). For releasing the securing mechanism between valve 12 and pliers elements 05, 07 there is provided in the present illustrative embodiment, in the area of the axial end of the pliers element 05, 07, a push button of the first type 14. By operating the push button of the first type 14 the connection between valve 12 and consequently pliers element 05, 07 can be released.

As can be seen from FIG. 1, push-button means of the first type 14 are provided on opposite sides of the two pliers elements 05 and 07. Thereby it is possible to operate both securing mechanisms of the first type in the sense of a one-handed operation, for example, by means of the index finger and the thumb, and to thereby release the connection between the valves 12 and the pliers elements 05, 07. In the present illustrative embodiment the grip elements 06, 08 are provided pivotable on the respective corresponding linkage parts 02, 03. The pivotable connection of the grip elements 06, 08 with the linkage parts 02, 03 is respectively accomplished via one pivot axis 15. For accomplishing a rigid connection between the grip elements 06, 08 and the linkage part 02, 03 there is provided in the area of the pivot axis 15 a locking mechanism (not shown). By the locking mechanism it is possible to released the rigid connection between the grip elements 06, 08 and the linkage parts 02, 03, whereby the grip elements 06, 08 are set free for pivoting about the pivot axis 15. A possible design of the locking mechanism is comprised therein, that these are provided in the form of spring engaging locking mechanism, whereby the grip elements 06, 08 are lockable in the position in which the rigid connection between the grip elements 06, 08 and the linkage parts 02, 03 is established. For releasing the locking mechanism a push button of the third type 16 is provided. In the area of the linkage part 02, 03 there is provided on the first side, with respect to the axis of rotation 04, an adjusting element 17. The adjusting element 17 is comprised of a set nut 18 and a threaded shaft 19. The threaded shaft 19 is pivotably connected with a first link part 02 and extends through an opening in the area of the second link part 03. The set nut is screwed onto the threaded shaft 19 on a side of the second link part 03 opposite to the first link part 02. By rotation of the adjusting nut 18 the link parts 02, 03 are more or less brought together, depending upon the position of the linkage nut 18 on the threaded shaft 19. In order to automatically open the linkage parts 02, 03 from a closed position, that is, in order to make possible a one-handed operation by the operator, a pressure spring 20 is provided on the threaded shaft 19 in the area between the linkage parts 02, 03.

FIG. 1b shows the vertebral distractor shown in FIG. 1a in the open position. In the open position the valves 12 as well as the pliers elements 05, 07 are spaced apart from each other. In order to make possible a parallel opening of the pliers elements 05, 07, a scissors part 21 is provided between the pliers elements 05, 07. It can further be recognized, that in the open position between the link parts 02, 03 in the area of the first side, with respect to the axis of rotation 04, are brought to bear against each other. In this position the maximum spread angle of the angular distractor is set or determined. It can further be recognized, that the set nut 18 is screwed far onto the threaded shaft 19.

Figure 2:
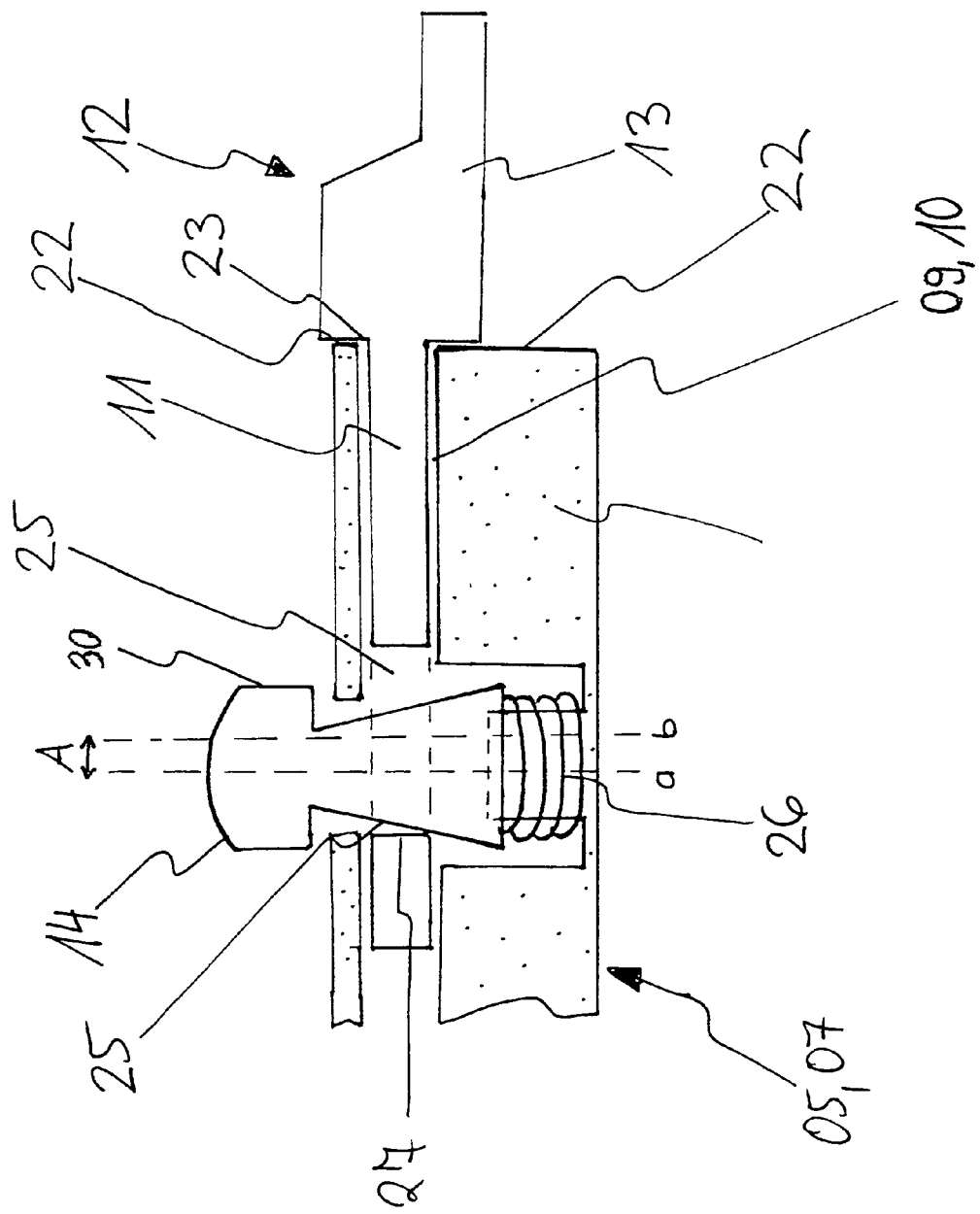
FIG. 2 a securing mechanism of first type in cross-section.

FIG. 2 shows a sectional enlargement of the pliers elements 05, 07 in the area of the free axial end with the valve 12 closed. As can be seen from FIG. 2, the engagement element 11 of the valve 12 is inserted in a recess 09, 10 of pliers elements 05, 07. The depth of insertion of the valve 12 in the recess 09, 10 of the pliers elements 05, 07 is determined by the contact between an abutment surface 22, which is formed by the face of the free axial end of the pliers elements 05, 07, as well as by a counter-surface 23 in the area of the valve 12. In the present embodiment the counter-surface 23 is formed by a step-like transition area between the jaw 13 and engagement element 11. Further in the area of the pliers elements 05, 07 a locking element 30 is provided. In the present illustrated example the locking element 30 forms one integral unit together with the push button of the first type 14. Further, the locking element 30 is moveable along its longitudinal axis a, which runs perpendicular to the direction of insertion of the engagement element 11 in the recess 09, 10 of the pliers elements 05, 07. In the connected condition, that is, in the condition in which the valve is rigidly however releaseably connected with the pliers elements 05, 07, the locking element 30 is brought into engagement with an arc shaped recess in the fork shaped engagement element 11 (see FIG. 3). In order to secure the valve 12 free of play on the pliers elements 05, 07, the locking element 30 is partially in the shape of a cone 25. In the connected condition on the one hand the abutment surface 22 and the counter-surface 23 come into contact, on the other hand the cone 25, on the basis of the force exerted by a spring 26, is brought to bear against a clamping surface 27 in the form of a hole shaped recess 24, which is set off from the longitudinal axis a of the locking element by the distance A, forwards with respect to the direction with insertion to an axis b running parallel through the center point of the hole-shaped recess 24. Thereby the valve 12 is tensioned-in essentially free of play and secured in the pliers elements 05, 07 on the basis of the abutment of the abutment surface 22 with the counter-surface 23 as well as by abutment of the clamping surface 27 with the cone 25 and on the basis of the force of the spring 26.

Figure 3:
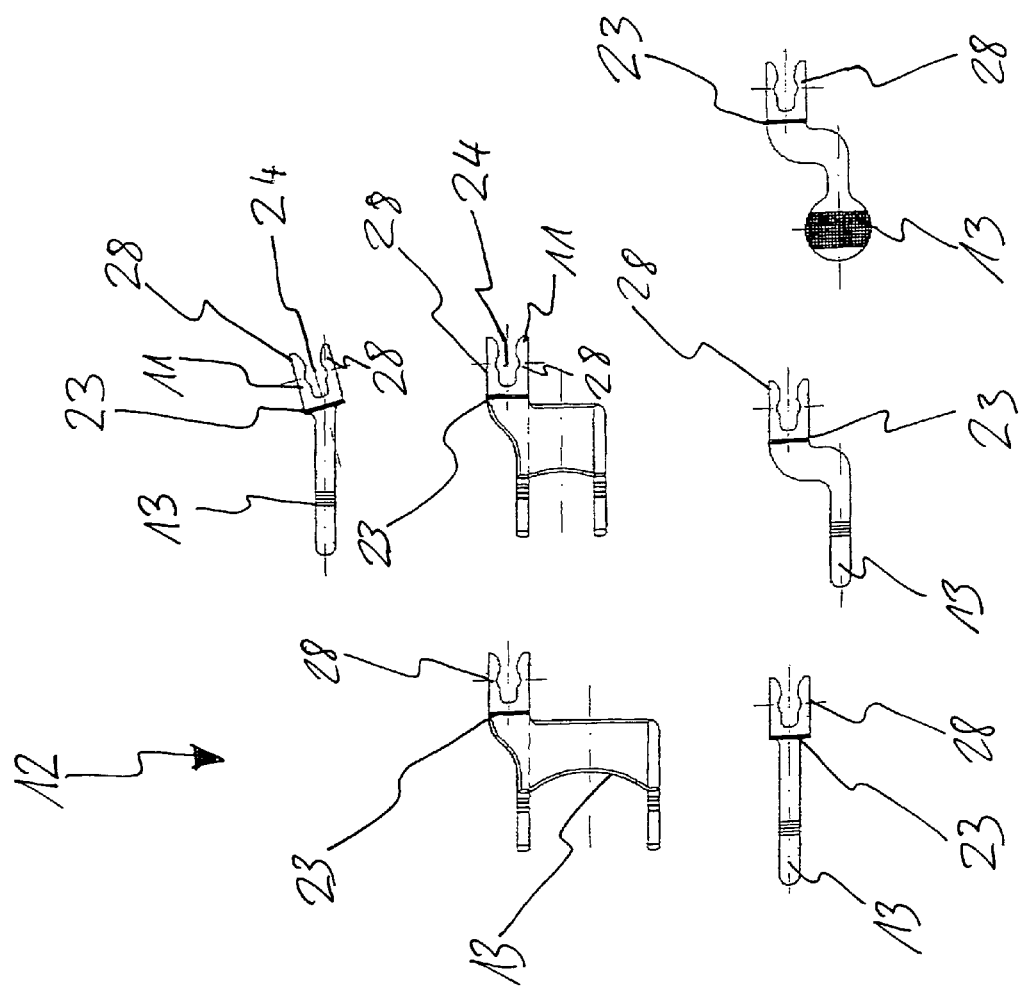
FIG. 3 different valves with various jaws in top view.

FIG. 3 shows different embodiments of valves 12. All valves essentially include the following elements. A jaw 13, which depending upon the purpose of employment can be variously designed. On the end of the jaw 13 connected with the engagement element 11 there is connected in the transition area between jaw 13 and engagement element 11 the counter-surface 23. In the present illustrative embodiment the engagement element 11 is fork shaped with two fork arms 28 as well as a hole-shaped widening or recess 24 in the area between the fork arms 28, which partially extends through between the fork arms 28.

Figure 4:
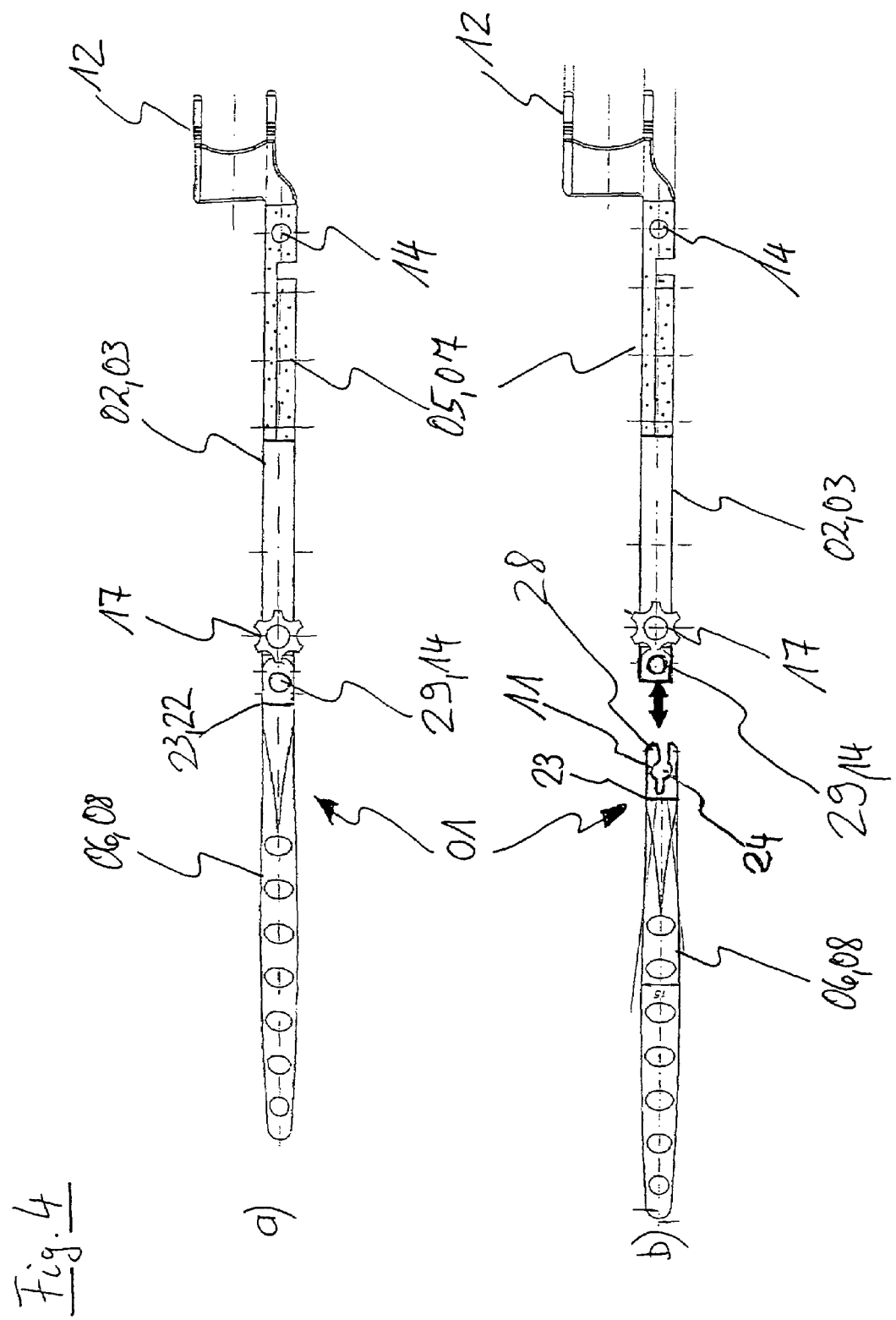
FIG. 4 a vertebral distractor with removable grip elements in secured and removed condition in top view.

FIG. 4 shows a vertebral distractor with removable grip elements 06, 08. For this a securing mechanism of the second type (not shown in greater detail in FIG. 4) is provided, which is operable via a push button of the second type 29. In the present illustrative embodiment the securing mechanism of the second type is provided just as the securing mechanism of the first type for securing the valves 12 on the pliers elements 05, 07. In FIG. 4b one recognizes the inventive vertebral distractor 01 with removed grip elements 06, 08. In the area of the axial end of the grip elements 06, 08 facing the linkage part 02, 03 is provided an appropriate engagement element 11 comprised of two fork arms 28 and a hole shaped recess 24. For connecting the grip elements 06, 08 with the linkage part 02, 03 the engagement element 11 of the grip elements 06, 08 is inserted in an insertion opening in the linkage part 02, 03 (not shown) and brought to bear and secured with its counter-surface 23 against the abutment surface 22, according to the description associated with FIG. 2. In the present illustrative embodiment the push button of the second type 29 is of the same design as the push button of the first type 14. This particularly simplifies the manipulation by the operator, since he need not readjust to each different kind of actuating mechanism.

Figure 5:
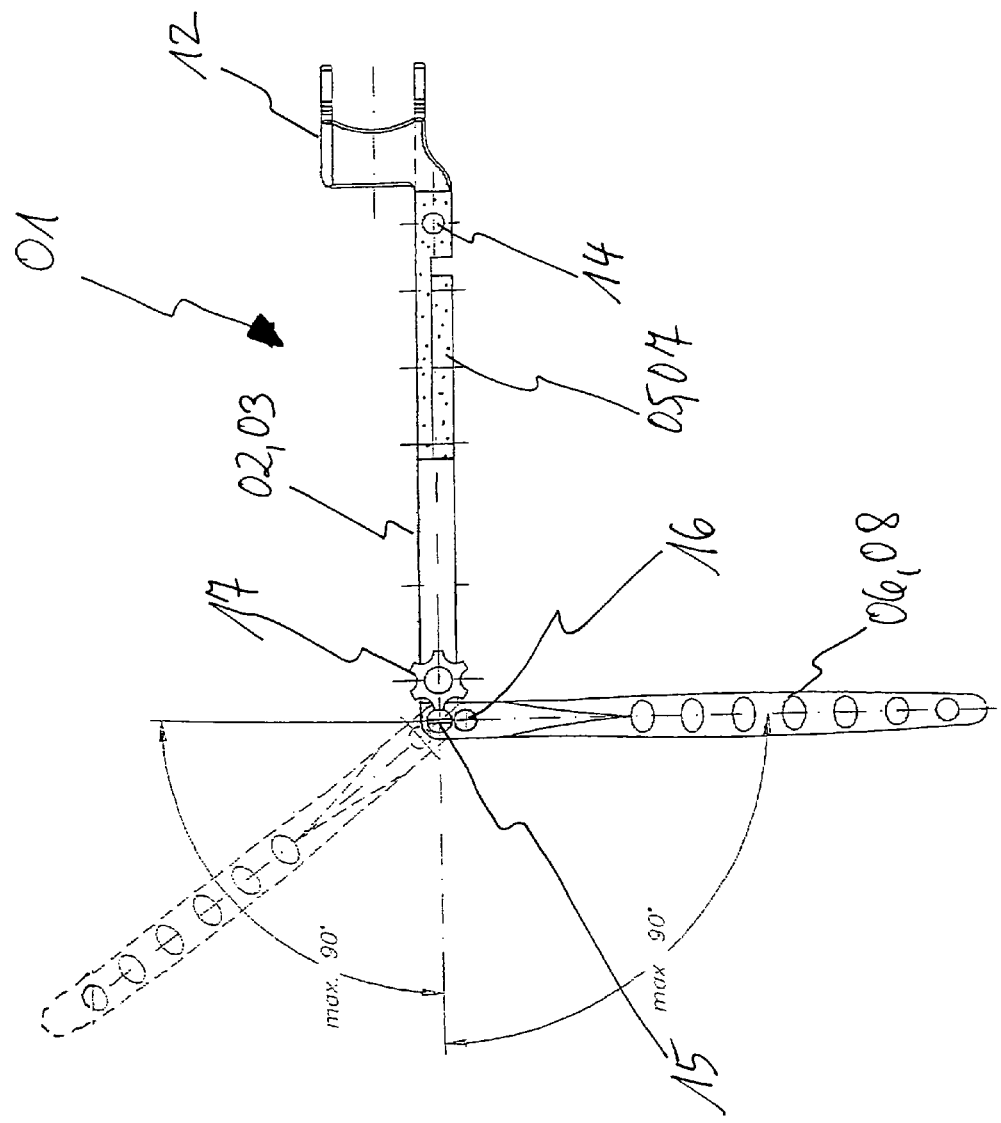
FIG. 5 a vertebral distractor with fold-back grip elements in folded back position in top view.

FIG. 5 shows an inventive vertebral distractor 01 with fold-back grip elements 06, 08 in top view. One recognizes the push button of the third type 16, which can be actuated to release the rigid connection between the grip elements 06, 08 and the linkage parts 02, 03. Thereby there is also the possibility, that the grip elements 06, 08 can be fixed in various angular positions of the linkage parts 02, 03 or also that the grip elements 06, 08 are connected rigidly only with one angular set position with the linkage part 02, 03 and after actuatuion of the push button of the third type 16 and releasing of the locking mechanism are freely pivotable.

Reference Number List

| | |
|---|---|
| 01 | Vertebral distractor |
| 02 | First link part |
| 03 | Second link part |
| 04 | Connecting pin |
| 05 | Pliers element (first link part) |
| 06 | Grip element (first link part) |
| 07 | Pliers element (second link part) |
| 08 | Grip element (second link part) |
| 09 | Recess (first link part) |
| 10 | Recess (second link part) |
| 11 | Engagement element |
| 12 | Valve |
| 13 | Jaw |
| 14 | Push button first type |
| 15 | Pivot axis |
| 16 | Push button third type |
| 17 | Adjusting element |
| 18 | Adjustment nut |
| 19 | Threaded shaft |
| 20 | Pressure spring |
| 21 | Scissors part |
| 22 | Abutment surface |
| 23 | Counter-surface |
| 24 | Hole shaped recess |
| 25 | Cone |
| 26 | Spring |
| 27 | Clamping surface |
| 28 | Fork arm |
| 29 | Push button second type |
| 30 | Locking element |

The invention claimed is:

1. A medical tool, comprising:
a first link part (2)
a second link part (3), wherein the first link part (2) is connected with the second link part (3) via a rotation axis (4), and
a grip element (6,8) and a pliers element (5,7) provided on each link part (2,3), wherein the link parts are operatively associated with each other,
wherein the two grip elements (6,8) are provided on a first side relative to the rotation axis (4) and the two pliers elements (5,7) are provided on a second side lying opposite to the first side,
wherein a valve (12) is seatable in the area of the free axial ends of a pliers element (5,7) and releasably connected by means of a first securing mechanism,
wherein a first push button (14) is provided on the first securing mechanism, via which the connection can be released,
wherein the first securing mechanism is essentially formed by an engagement element (11) as well as by a locking element (30) in operative association with the push button of the first type (14), wherein the locking element (30) is held in the locking position by a spring element (26),
wherein a maximal insertion depth is defined by the contact of an abutment surface (22) of the pliers element (5,7) with a counter-surface (23) of the valve (12), and
wherein the counter-surface (23) of the valve (12) is mechanically urged against the abutment surface (22) of the pliers element (5,7) by a force acting in the insertion direction between locking element (30) and engagement element (11).

2. A medical tool according to claim 1, wherein the first push button (14) is provided on the pliers element (5,7) or the valve (12).

3. A medical tool according to claim 1, wherein the engagement element (11) is provided on the valve (12), and that the first push button (14) is provided on the locking element (30) and the spring element (26) is provided on the pliers element (5,7).

4. A medical tool according to claim 3, wherein the first push button (14) and the locking element (30) form one integral unit.

5. A medical tool according to claim 1, wherein the valve (12) is insertable in a recess (9, 10) of the pliers element (5,7) essentially by means of the engagement element (11).

6. A medical tool according to claim 1, wherein the engagement element (11) is in the form of a longitudinally directed fork width an arc shaped segment (24), and that the locking element (30) is at least partially in the shape of a cone (25),
wherein the locking element (30) is moveable perpendicular to the insertion direction of the fork shaped engagement element (11),
wherein when the counter-surface (23) lies against the abutment surface (22) of the cone (25) and is partially operably engaged with a clamping surface (27) of the arc shaped recess (24), and wherein the longitudinal axis (a) of the locking element (30) is provided set off relative to the center point axis (b) of the arch shaped segment (24) in the insertion direction.

7. A medical tool according to claim 1, wherein at least one grip element (6,8) is releasably secured by means of a second securing mechanism on the linkage part (2,3).

8. A medical tool according to claim 7, wherein a second push button (29) is provided on the second securing mechanism, by means of which the connection is releasable.

9. A medical tool according to claim 7, wherein the second securing mechanism is the same as the first securing mechanism.

10. A medical tool according to claim 1, wherein at least one grip element (6, 8) is pivotably connected with the linkage part (2,3).

11. A medical tool according to claim 10, wherein a locking mechanism is provided, which can be moved from a first position, in which the grip element (6,8) and the linkage part (2,3) are pivotably relative to each other, can be brought to a second position, in which the grip element (6,8) and the linkage part (2,3) are rigidly connected with each other.

12. A medical tool according to claim 11, wherein the locking mechanism is operable by means of a third push button (16).

13. A medical tool according to claim 1, wherein two push buttons are provided on opposing sides of the two grip elements (6,8) or the linkage part (2,3).

14. A medical tool according to claim 13, wherein the push buttons are of the same design.

15. A medical tool according to claim 1, wherein the degree of opening of the linkage parts (2,3) to each other is settable by a set element (17).

16. A medical tool according to claim 15, wherein the set or adjustment element (17) is provided in the area of the linkage part (2,3) and connects these with each other.

17. A medical tool according to claim 16, wherein the adjusting element (17) is an adjusting nut (18) and a threaded shaft (19).

18. A medical tool according to claim 1, wherein between the linkage parts (2,3) a compression spring (20) is provided, via which the linkage parts (2,3) are pressed against each other in the area of the pliers element (5,7).

19. A medical tool according to claim 1, wherein in the area of the pliers element (5,7) a scissors part (21) is provided, by means of which the two pliers elements (5,7) are spreadable in parallel relative to each other.

20. Medical tool according to claim 1, wherein the medical tool is a vertebral distractor.

21. Medical tool according to claim 1, wherein the grip is removable.

22. A medical tool comprising:
a first link part (2)
a second link part (3), wherein the first link part (2) is connected with the second link part (3) via a rotation axis (4), and
a grip element (6,8) and a pliers element (5,7) provided on each link part (2,3), wherein the link parts are operatively associated with each other,
wherein the two grip elements (6,8) are provided on a first side relative to the rotation axis (4) and the two pliers elements (5,7) are provided on a second side lying opposite to the first side, and
wherein a valve (12) is seatable in the area of the free axial ends of a pliers element (5,7) and releasably connected by means of a first securing mechanism,
wherein a first push button (14) is provided on the securing mechanism of the first type, via which the connection can be released,
wherein each grip element is connected with the corresponding link part via a second rotation axis by means of a second securing mechanism; and
wherein the grip elements pivot about the second rotation axis.

23. A medical tool comprising:
a first (2) and a second link part (3),
wherein the first link part (2) is connected with the second link part (3) via a rotation axis (4),
wherein grip elements (6, 8) and a pliers elements (5, 7) are provided on each link part (2,3), which parts are operatively associated with each other, and wherein the two grip elements (6, 8) are provided on a first side relative to the rotation axis (4) and the two pliers elements (5, 7) are provided on a second side opposite to the first side,
wherein the grip elements (6, 8) are seatable in the area of the free axial ends of the linkage parts (2, 3) and releasably connected by means of a second securing mechanism,
wherein on the securing mechanism of the second type a second push button (29) is provided, via which the connection is releasable,
wherein the securing mechanism of the second type is essentially formed by an engagement element (11) as well as by a locking element in operative association with the push button of the second type (29), wherein the locking element is held in the locking position by a spring element,
wherein a maximal insertion depth is defined by the contact of an abutment surface of the linkage part (2, 3) with an opposing or counter-surface of the grip element (6, 8), and
wherein the counter-surface of the grip element (6, 8) is mechanical urged against the abutment surface of the linkage part (2, 3) by a force acting in the insertion direction between locking element and engagement element.

24. A medical tool according to claim 23, wherein the second push button (29) is provided on a linkage part (2, 3) or on a grip element (6, 8).

25. A medical tool according to claim 23, wherein two push buttons (14) are provided on opposing sides of the two linkage parts (2, 3).

26. A medical tool according to claim 23, wherein the engagement element is provided on a grip element (6, 8), and that the second push button (29) and the locking element and the spring element are provided on the linkage part (2, 3).

27. A medical tool according to claim 26, thereby characterized, that the second push button (29) and the locking element form one integral unit.

28. A medical tool according to claim 23, wherein the grip part is insertable in a recess in the linkage part (2, 3) essentially via the engagement element.

29. A medical tool according to claim 23, wherein the engagement element is in the form of a longitudinally directed fork width an arc shaped segment, and that the locking element is in the shape of a cone, and whereby the locking element is moveable perpendicular to the insertion direction of the fork shaped engagement element, wherein when the counter-surface lies against the abutment surface, the cone is operably engaged with a clamping surface of the arc shaped recess, and wherein the longitudinal axis of the locking element is provided offset relative to the center point axis of the arch shaped segment in the insertion direction.

* * * * *